ns011468402B2

(12) United States Patent
Yasuda

(10) Patent No.: US 11,468,402 B2
(45) Date of Patent: Oct. 11, 2022

(54) ARTICLE MANAGEMENT SYSTEM, METHOD AND COMPUTER PROGRAM

(71) Applicant: SILVACOMPASS Inc., Hamamatsu (JP)

(72) Inventor: Haruhiko Yasuda, Shizuoka (JP)

(73) Assignee: SILVACOMPASS INC., Shizuoka (JP)

( * ) Notice: Subject to any disclaimer, the term of this patent is extended or adjusted under 35 U.S.C. 154(b) by 262 days.

(21) Appl. No.: 16/785,144

(22) Filed: Feb. 7, 2020

(65) Prior Publication Data

US 2020/0334621 A1 Oct. 22, 2020

(30) Foreign Application Priority Data

Dec. 17, 2018 (JP) .............................. JP2018-235374

(51) Int. Cl.
| | |
|---|---|
| *G06Q 30/02* | (2012.01) |
| *G06Q 10/08* | (2012.01) |
| *B65G 1/04* | (2006.01) |
| *G16H 40/20* | (2018.01) |

(52) U.S. Cl.
CPC ............ *G06Q 10/087* (2013.01); *B65G 1/04* (2013.01); *G06Q 30/0241* (2013.01); *G06Q 30/0281* (2013.01); *G16H 40/20* (2018.01)

(58) Field of Classification Search
CPC ............ G06Q 10/087; G06Q 30/0241; G06Q 30/0281; G06Q 30/02; G06Q 30/0207; G06Q 30/0254; G06Q 10/067; G06Q 30/0246; B65G 1/04; B65G 1/1371; G16H 40/20; G16H 20/30; G16H 40/63
See application file for complete search history.

(56) References Cited

U.S. PATENT DOCUMENTS

| | | | | |
|---|---|---|---|---|
| 5,971,273 A | * | 10/1999 | Vallaire | G07F 9/105 235/381 |
| 6,710,800 B1 | * | 3/2004 | Park | H04N 1/00222 348/207.11 |
| 10,127,514 B2 | * | 11/2018 | Napoli | G06Q 10/083 |

(Continued)

FOREIGN PATENT DOCUMENTS

| | | |
|---|---|---|
| JP | 2002-291847 A | 10/2002 |
| JP | 2004-035143 A | 2/2004 |

(Continued)

OTHER PUBLICATIONS

Method and Apparatus for integrating Physical Location in Server Management (English (United States)), The IP.com Prior Art Database, Apr. 27, 2012 (Year: 2012).*

*Primary Examiner* — Marilyn G Macasiano
(74) *Attorney, Agent, or Firm* — WCF IP

(57) ABSTRACT

Provided are: a rack having a plurality of stages of storage units storing articles; a display device attached to the rack; and a management device configured to be capable of communicating with the display device and instruct the display device to display information on an article stored in the rack to which the display device is attached. The display device is a display that is capable of displaying image data relating to the article stored in the arranged rack. The management device displays and outputs image data on an article that needs to be taken out from the rack or stored in the rack and position information of a storage unit of the rack relating to the article according to instruction information.

9 Claims, 5 Drawing Sheets

(56) References Cited

U.S. PATENT DOCUMENTS

2008/0091574 A1* 4/2008 Hamaji ................ G06Q 10/087
    705/28
2016/0355338 A1* 12/2016 Kazama ............... B65G 1/1378

FOREIGN PATENT DOCUMENTS

| | | | |
|---|---|---|---|
| JP | 2007-289536 A | 11/2007 | |
| JP | 2017-174146 A | 9/2017 | |
| JP | 6330883 B2 * | 5/2018 | ............. B65G 1/137 |
| JP | 2018-188235 A | 11/2018 | |

* cited by examiner

ARTICLE MANAGEMENT SYSTEM, METHOD AND COMPUTER PROGRAM

BACKGROUND

Technical Field

The present invention relates to a mechanism configured to store and display an article on a rack, or take out an article. In particular, the present invention relates to a mechanism suitable for storing and taking out (picking) a medicine at a dispensing pharmacy and for storing and displaying a product at a general store and the like.

Related Art

Conventionally, various mechanisms have been proposed to take out many articles from a rack in which a large number of products are stored, and to store and display articles on the rack.

As one example, in order to output a message when selecting a medicine to call attention and prevent a dispensing error of the medicine beforehand, there is proposed a mechanism for taking out the medicine that is capable of preventing a mistake in a medicine to be used or a use amount thereof by causing a medicine storage device having an opening, configured to take in and out a medicine stored in a medical institution, to output medicine information on the medicine by a voice, a character, or an image, to detect that the opening has been opened, to read out the corresponding medicine information from a memory unit, and to output the read medicine information from a speaker or the like (JP 2002-291847 A).

In addition, in order to improve the efficiency and accuracy of picking a medicine and reliably reduce a picking mistake, there is proposed a mechanism configured to guide a dispenser using lamps in which multiple drug cabinets of a medicine rack are provided with the lamps and quantity display units that display the number of medicines to be picked, an ID of each dispenser is registered and a specific color is specified, a lamp of an ID color of the drug cabinet that needs to be first picked by a dispenser specified for each prescription is caused to blink and all lamps of subordinated drug cabinets are turned on, a lamp of the drug cabinet of the next order is switched from lighting to blinking when the picking from the first drug cabinet is finished, and such order of the drug cabinet to be switched from lighting to blinking is determined such that a movement distance of the dispenser becomes the shortest (JP 2007-289536 A).

In order to improve the efficiency of an operation of picking a drug during a dispensing operation, there is proposed a mechanism in which a marker reading unit reads a marker provided corresponding to a drug rack, a drug reading unit 23 reads a drug code configured to identify a type of the drug, and a different image is displayed on a display unit depending on whether or not a drug code of a drug placed at a position has been read by the drug reading unit to be superimposed on the position where the drug to be prescribed has been placed on a drug rack corresponding to the marker read by the marker reading unit, the position on a landscape that can be seen through a head-mounted display (JP 2017-174146 A).

SUMMARY

However, conventionally, there is a case where it is difficult to collate a product that a user is actually looking for with a trademark indicated by a lamp if a color of the lamp, a label, a bar code, and the like is used to indicate a position of the product. Therefore, it is difficult to determine whether a product actually obtained by the user is the same as the instructed product.

In addition, in the case of using a fixed device as in the related art, when sizes of racks vary depending on manufacturers or types, it is necessary to replace the device for each rack in the case of changing the device such as the lamp because a size of the device does not match the size of the rack, so that it is difficult to respond flexibly to changes in rack size.

In addition, when the devices such as the lamps are installed at each rack position, there is a problem that the number of the devices is large and the cost for introduction is high. In addition, when a wearable terminal such as the head-mounted display is used, there is a problem that it is difficult to constantly wear the terminal or a setting is required by a user.

Conventionally, a position of a product stored in the rack can be indicated by the lamp or the like, but there is no idea of using the position of the product when storing an article in the rack. For this reason, there is a case where even highly related articles are stored in distant places because the relation between each article is not known in the case of storing an article in the rack.

Therefore, the present invention has been made to solve the above problems, and an object thereof is to provide a mechanism that is easily attachable to and detachable from a rack and enables a user to confirm any position of the rack where a desired article is stored. Another object is to provide a mechanism capable of providing appropriate information even in the case of storing an article in the rack.

In order to achieve the above objects, an article management system according to one aspect of the present invention includes: a rack having a plurality of stages of storage units storing articles; a display device attached to the rack; and a management device configured to be capable of communicating with the display device and instruct the display device to display information on an article stored in the rack to which the display device is attached, wherein the display device is a display that is capable of displaying image data relating to the article stored in the rack, and the management device displays and outputs image data on an article that needs to be taken out from the rack or stored in the rack and position information of a storage unit of the rack relating to the article according to instruction information.

The display device may be arranged to straddle a plurality of the racks, and be capable of displaying an article that has been stored or needs to be stored in each of the racks in an area corresponding to the rack on the display device arranged to straddle.

The rack may be a product display rack in a store, and the display device may further display advertisement information on a product displayed on the rack to which the display device is attached.

The management device may be capable of receiving information on an instruction from an operation device held by a clerk, and display and output image data on an article that needs to be taken out from the rack or stored in the rack and position information of a storage unit of the rack relating to the article based on the instruction from the operation device.

In addition, the article management system may further include an analysis unit that measures an operation time of an operation of taking out or storing the article from the rack, performs analysis of data on the operation time, and performs a process of reflecting a result of the analysis to order in which the article is to be taken out from the rack or order in which the article needs to be stored next.

An article management method according to one aspect of the present invention is a method performed by a rack having a plurality of stages of storage units storing articles, a display device attached to the rack, and a computer configured to be capable of communicating with the display device and instruct the display device to display information on an article stored in the rack to which the display device is attached, the method causing the computer to make a display, capable of displaying image data relating to the article stored in the rack, display and output image data on an article that needs to be taken out from the rack or stored on the rack and position information of a storage unit of the rack relating to the article.

The display device may be arranged to straddle a plurality of the racks, and display an article that has been stored or needs to be stored in each of the racks in an area corresponding to the rack on the display device arranged to straddle.

The rack may be a product display rack in a store, and the display device may display advertisement information on a product displayed on the rack to which the display device is attached.

The management device may be capable of receiving information on an instruction from an operation device held by a clerk, and display and output image data on an article that needs to be taken out from the rack or stored in the rack and position information of a storage unit of the rack relating to the article based on the instruction from the operation device.

In addition, the method may further include a process of measuring an operation time of an operation of taking out or storing the article from the rack, performing analysis of data on the operation time, and performing a process of reflecting a result of the analysis to order in which the article is to be taken out from the rack or order in which the article needs to be stored next.

A computer program according to one aspect of the present invention is a computer program that causes a rack having a plurality of stages of storage units storing articles, a display device attached to the rack, and a computer, configured to be capable of communicating with the display device and instruct the display device to display information on an article stored in the rack to which the display device is attached, to function as an article management device, the computer program causing the computer to make a display, capable of displaying image data relating to the article stored in the rack, display and output image data on an article that needs to be taken out from the rack or stored on the rack and position information of a storage unit of the rack relating to the article.

According to this invention, it is possible to easily perform attachment and detachment with respect to the rack, and the user can visually confirm any position of the rack where the desired article is stored. In addition, as another effect, the appropriate information can be provided even in the case of storing an article in the rack. As a result, it is possible to provide the mechanism capable of providing the information on the article such that the operation can be performed efficiently in both the cases of taking out and storing the article.

DETAILED DESCRIPTION

According to embodiments of the invention, a display is provided at an upper end of a rack configured to store an article such that a position of the article stored in the rack, the content of the article, and the like can be displayed on the display.

Such a display may be arranged to straddle a plurality of the racks. In this case, at a display position on the display corresponding to a position of each rack, an article stored in the corresponding rack at the position and a storage position and the content thereof may be displayed.

In addition, by adopting this configuration, even in the case of storing an article on a rack, it is possible to instruct a position for storing the article such that the article is stored at the position with high efficiency according to a use state of the article, a sales situation at a store, and the like.

Further, when applied to a product display rack, it is also possible to guide a general consumer about a product stored in the product display rack by displaying the product stored on the product display rack in a store or the like on the display on the rack. Then, it is also possible to display product information on the display when a customer near the rack is recognized with a mobile terminal in conjunction with the mobile terminal (such as a smartphone) owned by the consumer and a product suitable for the recognized customer is stored in the product display rack.

First Embodiment

Example of Application as Rack for Dispensing Pharmacy

In this embodiment, it is possible to eliminate a mistake at the time of taking out a medicine and the like and a mistake at the time of storing an article on a rack and realize efficient storage on the rack by associating a prescription database of a computer with a position indication display attached to the rack. Then, an operation time can be measured by performing an operation in accordance with an instruction of a system, and labor saving can be achieved by estimating the operation time using this function.

Figure 1:
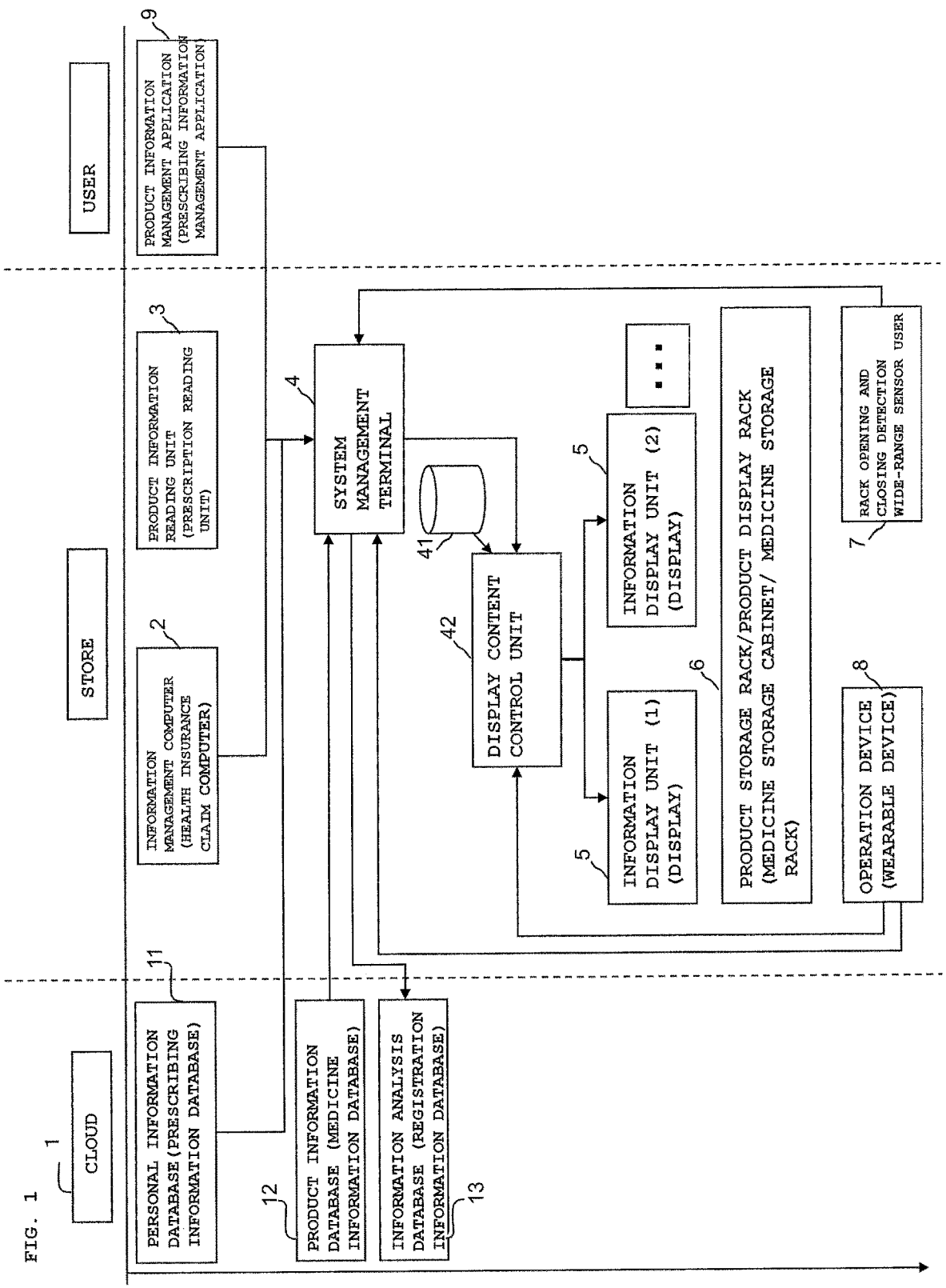
FIG. 1 is a diagram schematically illustrating a system configuration according to an embodiment of the invention.

FIG. 1 illustrates a configuration of a first embodiment.

In FIG. 1, the system of the present embodiment includes: a cloud computing (hereinafter, referred to as a cloud) 1; a store-side information management computer 2; a product information reading unit 3; a system management terminal 4; a display 5 as an information display unit; a storage rack 6 such as a product storage rack or a product display rack; a rack opening and closing sensor 7; an operation device 8; and a product information management terminal 9.

The cloud 1 has a personal information database 11 storing user's personal information and prescription data, a product information database 12 such as a medicine, and an information analysis database 13 storing information registered from the system management terminal 4 and information statistically analyzed by the cloud 1 based on the registered information.

In this example, the information management computer is a computer that manages a health insurance claim (medical service fee statement) information.

The information management computer 2 can create a health insurance claim of a pharmacy.

The product information reading unit 3 is a means for reading information such as a prescription brought by a patient. This product information reading unit 3 can be configured using, for example, a bar code reader in the case where the prescription data is bar-coded, software such as a scanner and an OCR in the case of reading a document itself, or a server managed by a medical institution and enabling connection and information acquisition from the outside.

The system management terminal 4 is a computer that controls product information and the like displayed on the display 5 attached to the rack 6.

The system management terminal 4 includes a display information memory unit 41 and a display content control unit 42.

The display information memory unit 41 can store product information which is displayed on the display 5 and output as text information or graphic information of a product.

The display content control unit 42 performs a process of determining which display content is to be displayed on which display 5 and which display area of the display 5. This determination process performs control according to information of a product (medicine) read by the product information reading unit 3 such that display is performed in an area on the display 5 corresponding to a position of a rack where the product has been stored.

The display 5 is a device configured to display and output the product information. The display 5 may be various displays such as a liquid crystal, an organic EL, and a wearable display such as a smart glass.

In this example, the display 5 straddles a plurality of (three in this example) racks 6 such that the single horizontally long display 5 is arranged at upper ends of the racks 6.

In this example, the display content control unit 42 performs control so as to allocate a left area, a central portion, and a right area of the display unit of the display 5 as a display area of the left rack 6, a display area of the central rack 6, and a display area of the right rack 6, respectively.

As a result, one display 5 can correspond to three racks.

In addition, the display 5 is detachable from the rack 6. Therefore, it is possible to easily associate the display with the rack by attaching the display 5 to a predetermined rack later and registering an address of the display 5.

The rack 6 is configured to store a product. An example of the rack 6 is illustrated in FIG. 2.

Figure 2:
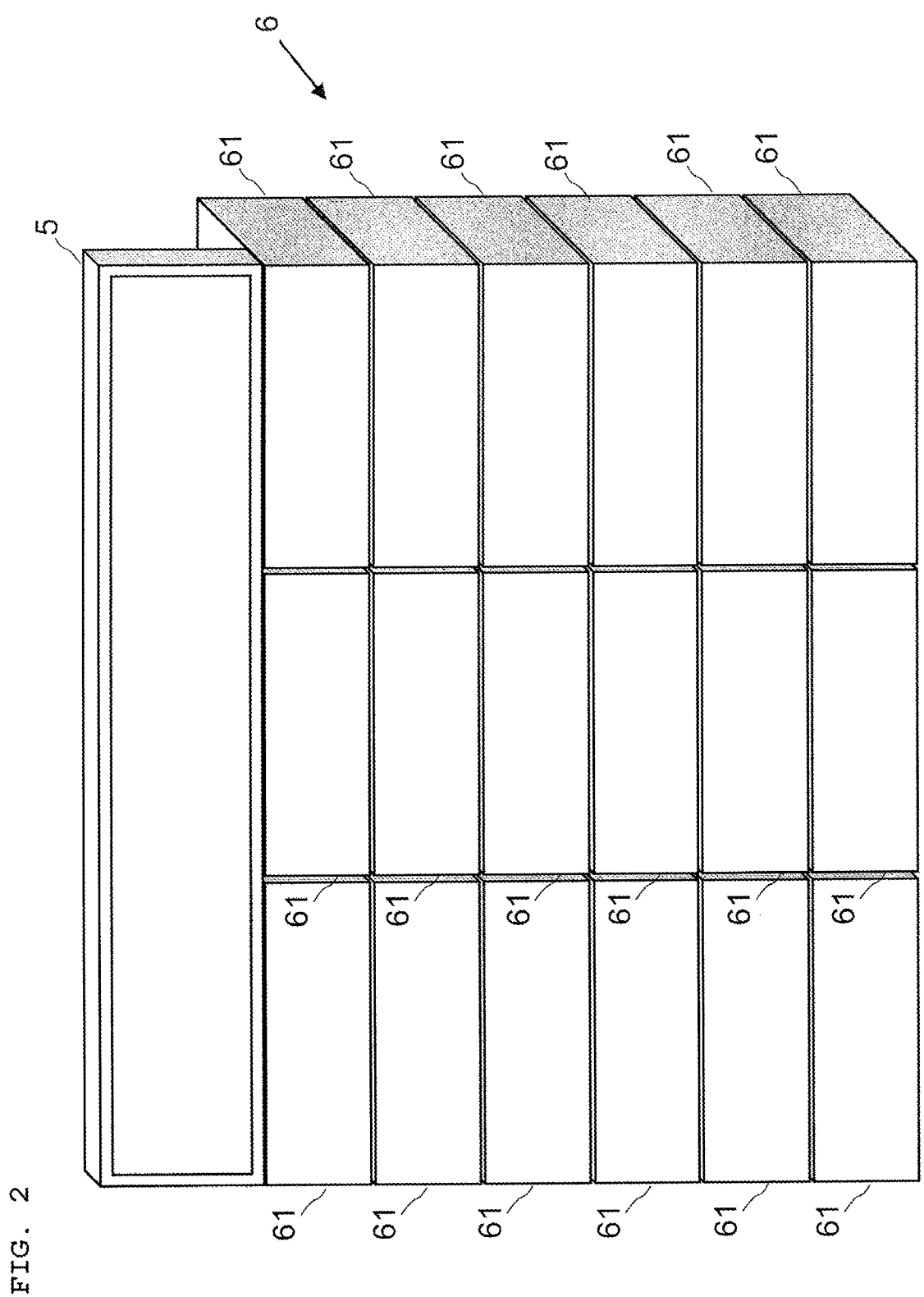
FIG. 2 is a perspective view schematically illustrating a rack according to an embodiment of the invention.

As illustrated in FIG. 2, one rack 6 has a plurality of stages in the vertical direction, and a case 61 as a storage unit configured to store an article (medicine) is arranged in each stage.

Note that the case 61 may be omitted, and only a side plate and a shelf board may be provided, or a door for opening and closing may be provided on the front surface.

The rack opening and closing sensor 7 is a sensor that detects whether each rack is open or closed. The rack opening and closing sensor 7 can be configured using an existing sensor such as an optical sensor or a magnetic sensor. The rack opening and closing sensor 7 is attached to each of the cases 61 of each of the racks 6 or a door, a shelf board, or the like of the rack storing the cases 61, and detects that each rack is open and closed.

Then, such opening or closing is notified to the system management terminal 4.

The operation device 8 is a device that transmits a signal to switch information displayed on the display 5.

When a user presses a predetermined button or the like after taking out one product, the signal is notified to the system management terminal 4 using short-range wireless communication with light or radio waves. As a result, the system management terminal 4 can perform a process of switching product information displayed on the specified rack 6 to product information on the next product according to the read prescription information.

Next, a processing flow of the first embodiment will be described.

Figure 3:
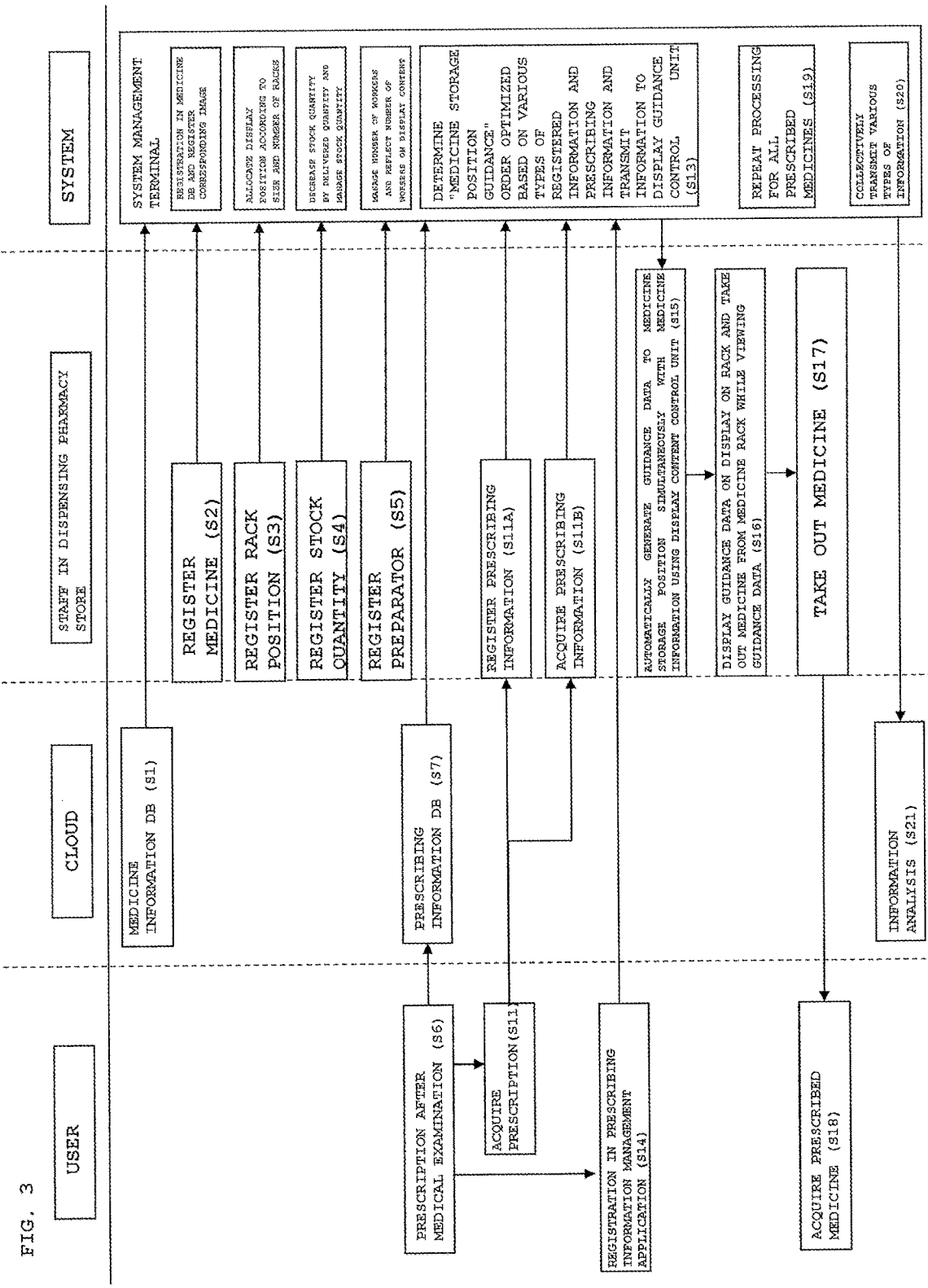
FIG. 3 is a processing flow according to a first embodiment.

In FIG. 3, processes, such as reading medicine data from a medicine information database of the cloud 1 (S1), registration of the read medicine data in the system management terminal 4 (S2), rack position information registration (S3) such as allocation of a display position of the display 5 according to a size of the rack 6 and the number of racks, registration of a stock quantity that has been decreased by a delivered quantity (S4), and a dispenser registration (S5) for registering dispenser information, are performed with respect to the system management terminal 4 as preliminary processes. The order of these processes is arbitrary.

In this state, when prescription information is registered by the hospital system after a patient (user) has been subjected to a medical examination (S6), the prescribing information is reflected in a prescribing information database of the cloud 1, and the prescribing information is acquired by inquiring the cloud 1 (S7).

In addition, prescription information is acquired by reading printed prescription information held by the patient (S11). As such an acquisition process, the prescription information may be registered manually in the information management computer 2 (S11A), or the prescription information may be acquired by scanning with the product information reading unit 3 (S11B).

As a result, the system management terminal 4 refers to a medicine DB, a display position allocation DB, a stock management DB, and the like registered in the system, and the display content control unit 42 generates guidance data to a medicine storage position that indicates medicine information included in the acquired prescription information, a rack where the medicine has been stored, and any stage of the rack where the medicine has been stored (S15). This guidance data calculates a shortest medicine acquisition route based on the pre-registered medicine storage information and prescribing information.

Then, the display content control unit 42 causes the display 5 installed on the rack storing the first medicine among the prescribed medicines to display and output the generated guidance data (S16).

Figure 4:
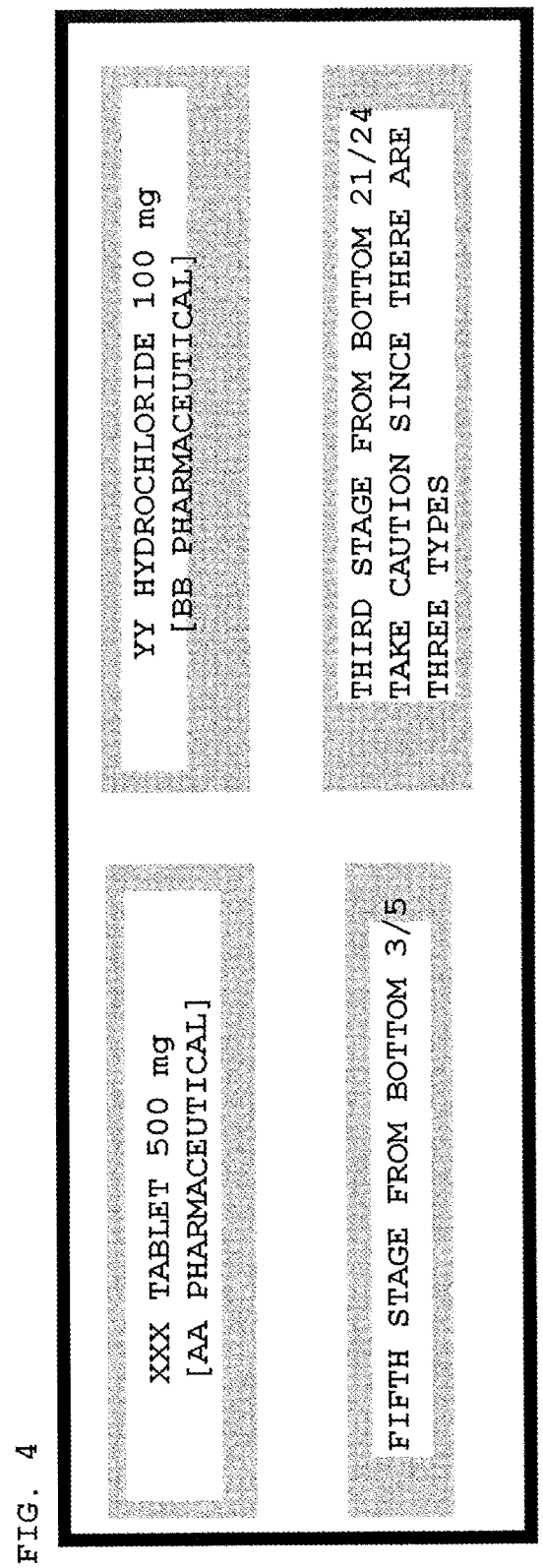
FIG. 4 is a view illustrating an example of a display state of a display according to an embodiment of the invention.

This example is illustrated in FIG. 4. In the example illustrated in FIG. 4, the display is divided into two areas A and B, and a rack A is arranged below the area A, and a rack B is arranged below the area B. When a medicine stored in the rack A is specified, image data of a package of the medicine is displayed in the upper part of the area A, and any stage of the rack A where the medicine has been stored and a number indicating the stage relative to the total number of stages (⅗) are displayed in the lower part. In this manner, when there are a plurality of racks, not only a display attached to a rack storing the medicine stored in the display position allocation database but also any area (the left side or the right side) of the display to which the rack belongs is identified, and the output is controlled to display information, such as medicine information (arbitrary such as a medicine name, an image of a package thereof, and a shape of a tablet itself) and position information where the medicine is stored (for example, text information such as the fifth stage or color information linked to a mark color affixed to the rack), on the display corresponding to the area.

In addition, an error in a medicine name or a standard and counting may be alerted using sound or displayed in an easy-to-understand and appropriate manner using text or a photograph to call attention. At the same time, an operation time may be measured, or a sensor or the like may be attached to each rack position (a shelf board or the like) to inspect (check) if the medicine has been taken out from a predetermined position in order to determine whether the medicine has been taken out from a wrong place.

As a result, a staff in a store can take out a specified amount of the medicine according to the prescription from the rack based on the displayed content of the display (S17).

As a result, the user can receive the prescribed medicine through the inspection or the like (S18).

In addition, when the staff in the store operates the holding operation device 8 after taking out one medicine, the system management terminal 4 refers to the medicine DB, the display position allocation DB, the stock management DB, and the like registered in the system similarly to the above-described S15 for the next prescribed medicine, and the display content control unit 42 generates guidance data to a medicine storage position that indicates information on the medicine, a rack where the medicine has been stored, and any stage of the rack where the medicine has been stored, and repeats the processes up to the following S19 in the same manner as described above (S18).

The processes from S15 to S19 are repeated for all the prescribed medicines.

During that time, the elapsed time from a start point to an end point of the processing performed based on the device operation is measured and stored.

When the processes are completed for all the medicines prescribed to the user, a message indicating the completion is displayed on the operation device 18 or a display on a predetermined rack, and the processing for one prescription is completed.

At a predetermined timing, the system management terminal 4 collectively uploads the medicines and the actually prescribed prescription data to the cloud 1 (S20). As a result, the cloud 1 registers the transmitted information in the information analysis database and analyzes the information (S21). Through this analysis of the cloud 1, statistical medicine use information on medicines that are frequently prescribed together and any medicine that is used for any disease is acquired, and analysis is performed based on this medicine use information such that the racks storing medicines and storage positions are efficiently set. For example, a medicine A and a medicine B are registered as medicines that need to be stored in adjacent rack positions on the same rack by statistically analyzing that the medicine A and the medicine B are often prescribed at the same time.

As a result, when allocating storage locations of the rack for the respective medicines, efficient allocation can be performed based on medicine material information, and it is possible to perform various types of analysis such as optimizing a storage method of a medicine storage cabinet, notifying the user of a waiting time by estimating the operation time, saving labor, and managing the stock by estimating a change of the number of medicines.

The operation time can be measured by performing an operation in accordance with an instruction of this system.

By using this function, labor saving can be achieved by estimating the operation time.

In addition, if the display is attached to the rack such that not only the name of the medicine (product) to be picked up but also the image of the package or the image of the tablet are displayed, it is possible to visually confirm whether or not the medicine (product) is correct rather than simply confirm the text.

Next, a second embodiment will be described. The second embodiment is an example in which the above-described example in the dispensing pharmacy is applied to a case where a product is arranged on a display rack in a general store such as a convenience store and a supermarket.

Figure 5:
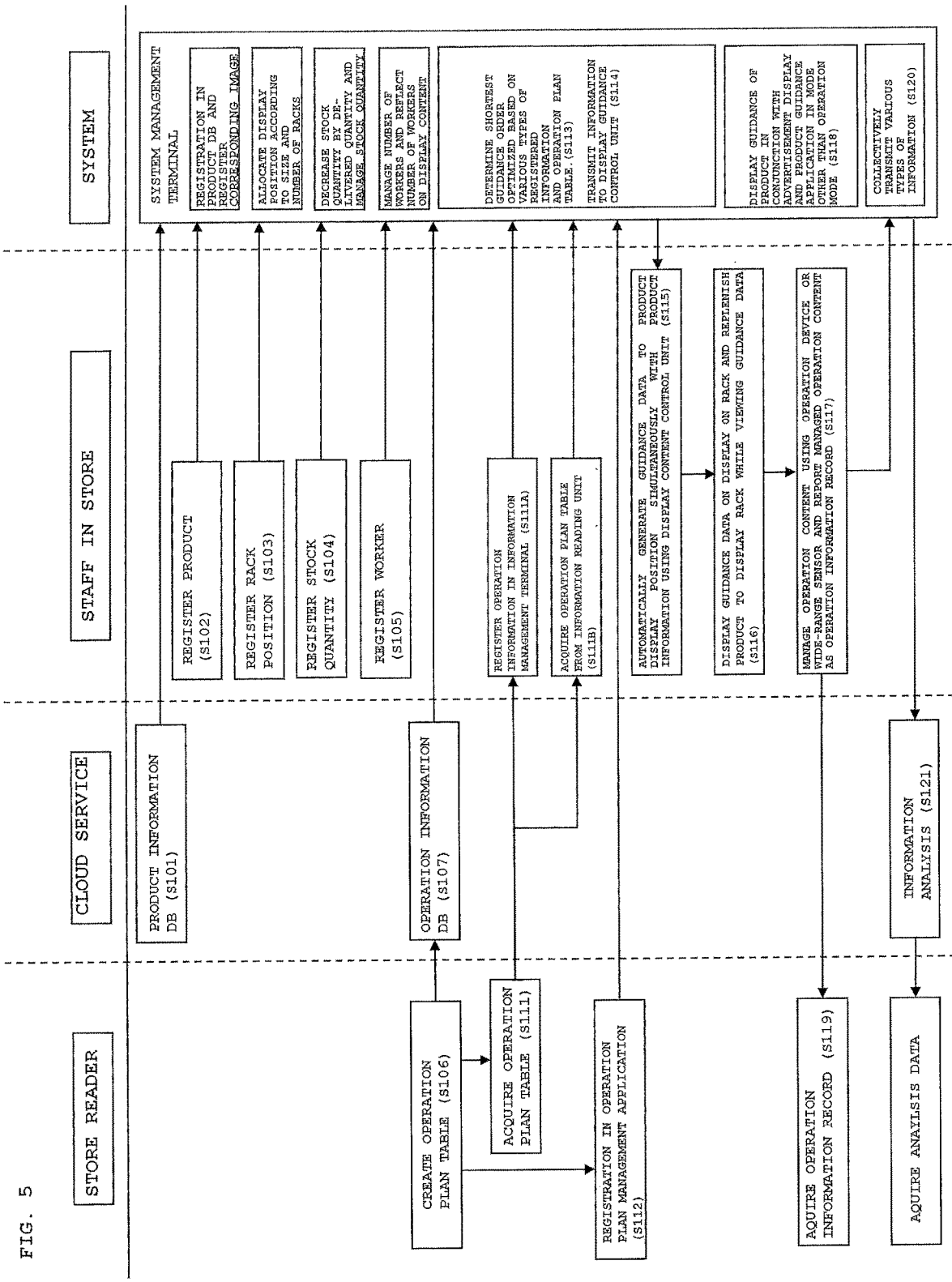
FIG. 5 is a processing flow according to a second embodiment.

In FIG. 5, processes, such as reading product data from a product information database of the cloud 1 (S101), registration of the product data in the system management terminal 4 (S102), rack position information registration (S103) such as allocation of a display position of the display 5 according to a size of the rack 6 and the number of racks, registration of a stock quantity that has been decreased by a delivered quantity (S104), and a worker registration (S105) for registering worker information, are performed with respect to the system management terminal 4 as preliminary processes. The order of these processes is arbitrary.

When operation plan information is created and registered by a store manager in this state (S106), the operation plan information is reflected in an operation information database of the cloud 1, and the operation plan information is acquired by inquiring the cloud 1 (S107).

Then, the store manager acquires an operation plan table by reading or the like (S111). As such an acquisition process, the operation plan information may be registered manually in the system management terminal 4 (S111A), or the operation plan information may be acquired by scanning with the information reading unit 3 (S111B).

In addition, the store manager registers the operation plan information in application software in his/her own mobile terminal (S112).

The system management terminal 4 determines the optimized shortest order up to a product display position based on registration information and the registered operation plan information in the above-described respective databases (S113), and transmits the generated information to a display guidance control unit (S114).

The system management terminal 4 refers to the product DB, the display position allocation DB, the stock management DB, and the like, and the display content control unit 42 generates guidance data to a product storage position that indicates product information included in the acquired operation plan information, a rack where the product has been stored, and any stage of the rack where the product has been stored (S115). This guidance data calculates a shortest product acquisition route based on pre-registered product storage cabinet information and operation plan information. Then, the display content control unit 42 causes the display 5, installed on the rack storing the first product of the prescribed products, to display and output the generated guidance data, and replenishes a product to the display rack while viewing the guidance data displayed on the display on the rack based on the display (S116).

When there are a plurality of racks, not only a display attached to a rack storing the product stored in the display position allocation database but also any position (the left side or the right side) of the display to which the rack belongs is identified, and the output is controlled to display information, such as product information and information on a storage position thereof (for example, the fifth stage) on the display corresponding to the position.

In addition, an error in a product name or a standard and counting may be alerted using sound or displayed in an easy-to-understand and appropriate manner using text or a photograph to call attention. At the same time, an operation time may be measured, or a sensor or the like may be attached to each rack position (a shelf board or the like) to inspect (check) if the medicine has been taken out from a predetermined position in order to determine whether the medicine has been taken out from a wrong place.

In addition, an operation content of the staff is managed by an operation device, a wide-range sensor, or the like, and transmitted to the system management terminal 4 as an operation information record (S117).

In addition, when the staff in the store operates the holding operation device 8 after taking out one product, the system management terminal 4 refers to the product DB, the display position allocation DB, the stock management DB, and the like registered in the system similarly to the above-described S115 for the next prescribed product, and the display content control unit 42 generates guidance data to a product storage position that indicates information on the product and a rack where the product needs to be displayed, and any stage of the rack, and repeats the processes up to the following S119 in the same manner as described above (S118).

During that time, the elapsed time from a start point to an end point of the processing performed based on the device operation is measured and stored.

Note that the operation information record may be transmitted a terminal of the store manager' such that the store manager can also share the operation information record (S119).

The processes from S115 to S119 are repeated for all the prescribed products.

When the display processing is completed for all the products, a message indicating the completion is displayed on the operation device 18 or a display on a predetermined rack, and the processing for one operation plan table is completed.

The system management terminal 4 collectively uploads operation result data including the operation plan information data and an operation measurement time to the cloud 1 at a predetermined timing (S120). As a result, the cloud 1 registers the transmitted information in the information analysis database and analyzes the information (S121). Through this analysis of the cloud 1, statistical product use information on products that are displayed and sold together is acquired, and analysis is performed based on this product use information such that the racks storing products and storage positions are efficiently set. For example, when a product A and a product B are displayed to be adjacent to each other on a rack, how much each of the products has been sold and where the rack is located when the product is sold are registered.

As a result, when allocating storage locations of the rack for the respective products, efficient allocation can be performed based on product material information, and it is possible to perform various types of analysis such as optimizing the product display, reduction in time and labor saving for the display operation, and managing the stock.

In addition, when a mode other than a display operation mode, advertisement information of a stored product can be displayed on the display of the display rack. Further, product information can be displayed on the display in conjunction with an application of a mobile terminal held by a customer user. For example, when the customer user inputs information on a product that the customer user is looking for to his or her mobile terminal, the system management terminal 4 may determine a position of a rack of the product and display a display position of the product on the display above the rack.

As a result, the invention can be also used as a mechanism for searching for the product that the general customer user is looking for and displaying a location of the product as well as simply used for the product display performed by the store staff.

Although the example in which the display is attached to the upper end of the rack has been described in each of the above embodiments, the attachment position of the display is arbitrary, and may be a position at a predetermined height.

What is claimed is:

1. An article management system comprising:
a plurality of racks arranged side-by-side having a plurality of stages of storage units for storing articles;
a display device arranged to extend over the plurality of racks and comprising a plurality of display areas; and
a management device configured to be capable of communicating with the display device and instruct the display device to display information on the articles stored in the racks,
wherein the display device is a display that is capable of displaying image data relating to the articles stored in the racks,
wherein the management device causes the display device to display on one of the display areas
article image data on an article that needs to be taken out from one of the racks or stored in one of the racks and
position information indicating a number of a storage unit of the racks relating to the article,
wherein the one of the display areas is over the one of the racks where the article is to be taken out from or stored in.

2. The article management system according to claim 1, wherein
the racks are product display racks in a store, and
the display device further displays advertisement information on a product displayed on the racks to which the display device is attached.

3. The article management system according to claim 1, wherein
the management device is capable of receiving information on an instruction from an operation device held by a worker, and
the management device outputs guidance data guiding to a position of a storage unit of a rack for a next article to be taken out or to be stored based on the instruction from the operation device.

4. The article management system according to claim 1, further comprising
an analysis unit that measures an operation time of an operation of taking out or storing the article from the racks, performs analysis of data on the operation time, and performs a process of reflecting a result of the analysis for an order in which the article is to be taken out from the racks or an order in which the article needs to be stored next.

5. An article management method for a plurality of racks arranged side-by-side having a plurality of stages of storage units for storing articles, a display device arranged to extend over the plurality of racks and comprising a plurality of display areas, and a computer configured to be capable of communicating with the display device and instruct the display device to display information on the articles stored in the racks, the method comprising with the computer, causing the display device, which is a display capable of displaying image data relating to the articles stored in the racks, to display on one of the display areas image data on an article that needs to be taken out from one of the racks or stored in one of the racks and position information indicating a number of a storage unit of the racks relating to the article, wherein the one of the display areas is over the one of the racks where the article is to be taken out from or stored in.

6. The article management method according to claim 5, wherein the racks are product display racks in a store, and the display device further displays advertisement information on a product displayed on the racks to which the display device is attached.

7. The article management method according to claim 5, wherein the management device is capable of receiving information on an instruction from an operation device held by a worker, and the management device outputs guidance data guiding to a position of a storage unit of a rack for a next article to be taken out or to be stored based on the instruction from the operation device.

8. The article management method according to claim 5, further comprising measuring an operation time of an operation of taking out or storing the article from the racks, performing analysis of data on the operation time, and reflecting a result of the analysis for an order in which the article is to be taken out from the racks or an order in which the article needs to be stored next.

9. A non-transitory computer readable medium that stores a computer program for controlling an article management system, the article management system comprising a plurality of racks arranged side-by-side having a plurality of stages of storage units for storing articles, a display device arranged to extend over the plurality of racks and comprising a plurality of display areas, and a computer, configured to be capable of communicating with the display device and instruct the display device to display information on the articles stored in the racks, to function as an article management device, the computer program, when executed by the computer, causing the computer to:

cause the display device, which is a display capable of displaying image data relating to the articles stored in the racks, to display on one of the display areas image data on an article that needs to be taken out from one of the racks or stored in one of the racks and position information indicating a number of a storage unit of the racks relating to the article, wherein the one of the display areas is over the one of the racks where the article is to be taken out from or stored in.

\* \* \* \* \*